United States Patent
Mark

(10) Patent No.: US 10,456,438 B2
(45) Date of Patent: Oct. 29, 2019

(54) COMPOSITION FOR TREATING PRURITUS

(71) Applicant: Kenneth Mark, Southampton, NY (US)

(72) Inventor: Kenneth Mark, Southampton, NY (US)

(*) Notice: Subject to any disclaimer, the term of this patent is extended or adjusted under 35 U.S.C. 154(b) by 275 days.

(21) Appl. No.: 15/217,721

(22) Filed: Jul. 22, 2016

(65) Prior Publication Data

US 2018/0021396 A1     Jan. 25, 2018

(51) Int. Cl.
| | | |
|---|---|---|
| *A61K 36/886* | (2006.01) | |
| *A61K 36/185* | (2006.01) | |
| *A61K 31/573* | (2006.01) | |

(52) U.S. Cl.
CPC ......... *A61K 36/886* (2013.01); *A61K 31/573* (2013.01); *A61K 36/185* (2013.01)

(58) Field of Classification Search
None
See application file for complete search history.

(56) References Cited

U.S. PATENT DOCUMENTS

| | | | | |
|---|---|---|---|---|
| 2002/0127256 A1* | 9/2002 | Murad | ............... | A61K 8/365 424/401 |
| 2010/0215726 A1* | 8/2010 | Roth | ............... | A61K 8/64 424/450 |
| 2014/0301964 A1* | 10/2014 | Ciccognani | ............... | A61K 8/37 424/70.1 |

OTHER PUBLICATIONS

Bernstein, JA. "Hydrocortisone" in Handbook of Allergic Disorders. p. 409. (Year: 2003).*

* cited by examiner

*Primary Examiner* — Amy L Clark
(74) *Attorney, Agent, or Firm* — Notaro, Michalos & Zaccaria P.C.

(57) ABSTRACT

A composition and method for treating itching, burning and discomfort of the skin and/or mucous membranes including the perianal and vaginal regions. The composition comprising therapeutically effective amounts of *Aloe barbadensis* leaf gel, deionized water, C12-15 alkyl benzoate, *Camellia sinensis* leaf extract, ceteareth-20, cetearyl alcohol, cetyl alcohol, ethylhexylglycerin, glycerin stearate, *Hamamelis virginiana* extract, *Helianthus annus* seed oil, PEG-100 stearate, petrolatum, phenoxyethanol, stearyl alcohol, tocopheryl acetate, Zemea propanediol and hydrocortisone.

4 Claims, No Drawings

COMPOSITION FOR TREATING PRURITUS

FIELD OF THE INVENTION

The present invention generally relates to the treatment of pruritus, more specifically relates to topical composition and method for alleviating itching, burning and discomfort of the skin and/or mucous membranes including the perianal and vaginal regions in humans.

BACKGROUND

"Pruritus" refers to an unpleasant sensation on the skin that urges to scratch or rub the area in order to obtain relief. Pruritus is commonly characterized by generalized and localized itching. Itching may be caused as a clinical manifestation of localized skin disorder, systemic disease, scratch reaction, insect bite, sunburn, wound healing and exposure to irritants such as plant toxins, chemicals, microbial proteins, and/or additional external mechanical, thermal and electrical stimuli. Common types of itching include anal itch, chemical itch, eczema, (including seborrheic dermatitis) pruritus dermatitis, diabetic skin itch, aging skin itch, foot-itch, jock itch, hives, dry winter skin itch and stress related scalp itch. Those who suffer from itch often note, persistent or recurrent attacks. Although usually occurring in the skin, pruritus can also occur in non-cutaneous sites such as mucous membranes. "Perianal itching" or "Pruritus ani" refers to the persistent itching and irritation of skin around the anus region. Perianal itching and burning not only causes physical discomfort but also results in distraction and socially awkward or embarrassing situations. Anal itching may be caused by chemical irritants in food, diarrhea, psoriasis, anal fissure, hemorrhoids, skin tags, diabetes, yeast infection and pinworm infection.

Current treatment options for localized pruritus including perianal itching involves the use of topical agents such as emollients, ointments and oral drugs such as steroids, anti-inflammatory agents, local anesthetics, antihistamines, thermal stimulation and Ultraviolet phototherapy. However, treatment with existing topical agents shows general but nonspecific benefit. Non-specific topical preparations including lotions, creams and oil-based ointments may provide softness and moisturizing effect on the dry skin, but causes an uncomfortable feeling and discomfort due to greasy nature of the preparation and soiling of garments. In addition, existing topical agents used for relieving perianal pruritus act slow and fail to provide complete cure from itching and burning.

Therefore, there is a need for an improved topical pharmaceutical preparation for providing rapid relief from pruritus by alleviating itching and burning in the perianal region of humans. There is also a need for improved composition and method for treating pruritus of the skin and/or mucous membranes including the perianal and vaginal regions in humans.

SUMMARY OF THE INVENTION

The present invention relates to a composition for treating itching, burning and discomfort of the skin and/or mucous membranes including the perianal and vaginal regions. The composition consisting essentially of *Aloe barbadensis* leaf gel, deionized water, C12-15 alkyl benzoate, *Camellia sinensis* leaf extract, ceteareth-20, cetearyl alcohol, cetyl alcohol, ethylhexylglycerin, glycerin stearate, *Hamamelis virginiana* extract, *Helianthus annus* seed oil, PEG-100 stearate, petrolatum, phenoxyethanol, stearyl alcohol, tocopheryl acetate, Zemea propanediol and hydrocortisone.

In an embodiment, the present invention relates to a composition for treating localized pruritus. The composition comprises hydrocortisone in an amount up to about 1 percent by weight and *Aloe barbadensis* leaf gel (0-50%), *Hamamelis virginiana* extract (0-50%), deionized water, C12-15 alkyl benzoate, *Camellia sinensis* leaf extract, ceteareth-20, cetearyl alcohol, cetyl alcohol, ethylhexylglycerin, glycerin stearate, *Helianthus annus* seed oil, PEG-100 stearate, petrolatum, phenoxyethanol, stearyl alcohol, tocopheryl acetate and Zemea propanediol in amounts up to 3 percent by weight.

In an embodiment, the present invention relates to a method for treating itching, burning and discomfort of the skin and/or mucous membranes including the perianal and vaginal regions. The method comprises administering topically a pharmaceutical composition consisting 0 to 50% by weight *Aloe barbadensis* leaf gel, 0 to 50% by weight *Hamamelis virginiana* extract, 0 to 3% deionized water, C12-15 alkyl benzoate, *Camellia sinensis* leaf extract, ceteareth-20, cetearyl alcohol, cetyl alcohol, ethylhexylglycerin, glycerin stearate, *Helianthus annus* seed oil, PEG-100 stearate, petrolatum, phenoxyethanol, stearyl alcohol, tocopheryl acetate, and Zemea propanediol; and 0 to 1% by weight hydrocortisone.

DETAILED DESCRIPTION OF PREFERRED EMBODIMENTS

The terms "active agent," "drug", "active compound" and "pharmacologically active agent" are used interchangeably herein to refer to a chemical material or compound which, when administered to humans, induces a desired pharmacologic effect. Included are derivatives and analogs of those compounds or classes of compounds specifically mentioned which also induce the desired pharmacologic effect.

"Pharmaceutically acceptable salt" refers to a salt of a compound, which possesses the desired pharmacological activity of the parent compound. Such salts include: acid addition salts, formed with inorganic acids; acid addition salts formed with organic acids; or salts formed when an acidic proton present in the parent compound is replaced by a metal ion, e.g., an alkali metal ion, aluminum ion; or coordinates with an organic base such as ethanolamine, and the like.

Pharmaceutically acceptable "carrier" or "carrier" is composed of materials that are present in pharmaceutical formulation other than the active ingredient. Carriers are considered safe and effective and may be administered to an individual without causing undesirable biological side effects. The term "carrier" includes, but is not limited to, excipients, diluents, binders, lubricants, disintegrators, fillers, gliding agent and coating compositions.

The present invention relates to a pharmaceutical composition for treating anal pruritus. The pharmaceutical composition comprises at least one active agent or its pharmaceutically acceptable salts thereof and at least one pharmaceutically acceptable carrier. The composition is used for rapidly alleviating external anal itching and burning in humans.

In an embodiment, the present invention relates to a composition for treating itching, burning and discomfort of the skin and/or mucous membranes including the perianal and vaginal regions. The composition consisting essentially of *Aloe* leaf gel, deionized water, C12-15 alkyl benzoate, Green tea leaf extract, ceteareth-20, cetearyl alcohol, cetyl alcohol, ethylhexylglycerin, glycerin stearate, Witch Hazel extract, Sunflower seed oil, polyethylene glycol(PEG)-100 stearate, petrolatum, phenoxyethanol, stearyl alcohol, tocopheryl acetate (Vitamin E), Zemea propanediol and hydrocortisone.

In an embodiment, the *Aloe* leaf gel of the composition is obtained from *Aloe barbadensis* leaves. Green tea leaf extract is obtained from *Camellia sinensis* leaves. Witch Hazel extract comprises an extract of *Hamamelis virginiana* and Sunflower seed oil is obtained from *Helianthus annus* seeds.

The present invention relates to a composition for treating localized anal pruritus. The composition comprises hydrocortisone in an amount up to about 1 percent by weight and *Aloe barbadensis* leaf gel, and *Hamamelis virginiana* extract are in amounts up to 50 percent by weight. Other components such as deionized water, C12-15 alkyl benzoate, *Camellia sinensis* leaf extract, ceteareth-20, cetearyl alcohol, cetyl alcohol, ethylhexylglycerin, glycerin stearate, *Helianthus annus* seed oil, PEG-100 stearate, petrolatum, phenoxyethanol, stearyl alcohol, tocopheryl acetate and Zemea propanediol are in amounts up to 3 percent by weight.

In another embodiment, the present invention relates to a method for treating itching, burning and discomfort of the skin and/or mucous membranes including the perianal and vaginal regions. The method comprises administering topically a pharmaceutical composition consisting 0 to 50% by weight *Aloe barbadensis* leaf gel, 0 to 50% by weight *Hamamelis virginiana* extract and 0 to 3% by weight deionized water, C12-15 alkyl benzoate, *Camellia sinensis* leaf extract, ceteareth-20, cetearyl alcohol, cetyl alcohol, ethylhexylglycerin, glycerin stearate, *Helianthus annus* seed oil, PEG-100 stearate, petrolatum, phenoxyethanol, stearyl alcohol, tocopheryl acetate, and Zemea propanediol; and 0 to 1% by weight hydrocortisone.

The composition is prepared in a form suitable for topical application on the skin surface of perianal region. The composition can be prepared in the form of cream, spray, lotion, solution, gel, emollient, ointment and aerosol form for application on the external perianal area of human body in order to alleviate itching.

EXAMPLE 1

In this exemplary embodiment, the composition of the present invention is formulated in the form of a topical cream, which comprises the active agent and pharmaceutically acceptable carriers in a specific percent by weight ratio as mentioned in Table 1.

TABLE 1

| Ingredient | Ratio (Percent by Weight) |
| --- | --- |
| Hydrocortisone | 0 to 1 |
| *Hamamelis virginiana* extract | 0 to 50 |

TABLE 1-continued

| Ingredient | Ratio (Percent by Weight) |
| --- | --- |
| *Camellia sinensis* leaf extract | 0 to 3 |
| Tocopheryl acetate (Vitamin E) | 0 to 3 |
| *Aloe barbadensis* juice | 0 to 50 |
| *Helianthus annuus* seed oil | 0 to 3 |
| Cetyl alcohol | 0 to 3 |
| Glycerin stearate | 0 to 3 |
| Ceteareth-20 | 0 to 3 |
| Stearyl alcohol | 0 to 3 |
| C12-15 alkyl benzoate | 0 to 3 |
| Cetearyl alcohol | 0 to 3 |
| Zemea propanediol | 0 to 3 |
| Phenoxyethanol | 0 to 3 |
| PEG-100 stearate | 0 to 3 |
| Ethylexylglycerin | 0 to 3 |
| Petrolatum | 0 to 3 |
| Aqua (deionized water) | 0 to 3 |

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A composition for treating itching, burning and discomfort of the skin and/or mucous membranes of the perianal and vaginal regions, the composition consisting essentially of *Aloe barbadensis* leaf gel, deionized water, C12-15 alkyl benzoate, *Camellia sinensis* leaf extract, ceteareth-20, cetearyl alcohol, cetyl alcohol, ethylhexylglycerin, glycerin stearate, *Hamamelis virginiana* extract, *Helianthus annus* seed oil, PEG-100 stearate, petrolatum, phenoxyethanol, stearyl alcohol, tocopheryl acetate, propanediol and hydrocortisone.

2. The composition of claim 1, wherein the composition is in the form of a lotion, cream, emollient, ointment, spray, aerosol or gel.

3. A method for treating itching, burning and discomfort of the skin and/or mucous membranes of the perianal and vaginal regions in a subject in need thereof comprising topically administering to the skin and/or mucous membranes of said subject an effective amount of a pharmaceutical composition consisting essentially of *Aloe barbadensis* leaf gel, deionized water, C12-15 alkyl benzoate, *Camellia sinensis* leaf extract, ceteareth-20, cetearyl alcohol, cetyl alcohol, ethylhexylglycerin, glycerin stearate, *Hamamelis virginiana* extract, *Helianthus annus* seed oil, PEG-100 stearate, petrolatum, phenoxyethanol, stearyl alcohol, tocopheryl acetate, propanediol and hydrocortisone.

4. The method of claim 3, wherein the pharmaceutical composition is in the form of a lotion, cream, emollient, ointment, spray, aerosol or gel.

* * * * *